United States Patent

Klocke et al.

(10) Patent No.: US 8,262,722 B2
(45) Date of Patent: Sep. 11, 2012

(54) ENDOPROSTHESIS

(75) Inventors: Bjoern Klocke, Zurich (CH); Johannes Riedmueller, Nuremberg (DE)

(73) Assignee: BIOTRONIK VI Patent AG, Baar (CH)

( * ) Notice: Subject to any disclaimer, the term of this patent is extended or adjusted under 35 U.S.C. 154(b) by 371 days.

(21) Appl. No.: 12/613,480

(22) Filed: Nov. 5, 2009

(65) Prior Publication Data

US 2010/0121432 A1   May 13, 2010

(30) Foreign Application Priority Data

Nov. 11, 2008 (DE) .......................... 10 2008 043 642

(51) Int. Cl.
*A61F 2/06* (2006.01)
(52) U.S. Cl. ..................................... 623/1.34
(58) Field of Classification Search ................. 623/1.15, 623/1.34, 1.42–1.46
See application file for complete search history.

(56) References Cited

U.S. PATENT DOCUMENTS

| | | | |
|---|---|---|---|
| 6,293,966 | B1 | 9/2001 | Frantzen |
| 2004/0015229 | A1 | 1/2004 | Fulkerson et al. |
| 2008/0033531 | A1* | 2/2008 | Barthel et al. ............... 623/1.15 |

FOREIGN PATENT DOCUMENTS

| | | |
|---|---|---|
| DE | 696 23 855 T2 | 6/1996 |
| DE | 698 38 256 T2 | 5/2008 |
| DE | 60 2004 10 347 T2 | 10/2008 |
| EP | 1886650 A1 | 2/2008 |
| WO | 0158384 A1 | 8/2001 |
| WO | 2004105642 A1 | 12/2004 |
| WO | WO 2006/096251 A2 | 9/2006 |
| WO | WO 2007/126768 A2 | 11/2007 |
| WO | WO 2007/133520 A2 | 11/2007 |
| WO | 2008101987 A1 | 8/2008 |
| WO | WO 2008/101987 A1 | 8/2008 |

OTHER PUBLICATIONS

European search report for application EP 09174331.0.
German Search Report for Priority Document DE 10 2008 043 642.9.

* cited by examiner

*Primary Examiner* — William H. Matthews
(74) *Attorney, Agent, or Firm* — Biotech Beach Law Group PC

(57) ABSTRACT

An endoprosthesis, in particular an intraluminal endoprosthesis, for example a stent, having a base body composed at least partially of a metallic material, and having a functional element which is attached to the base body or imbedded therein and which contains material that is radiopaque and/or X-ray opaque and has a different material composition, at least in a portion of its volume, compared to the material of the base body. To avoid contact corrosion and undesired corrosion, the functional element is provided with a barrier layer which electrically insulates the radiopaque and/or X-ray opaque material from the base body.

14 Claims, 3 Drawing Sheets

ENDOPROSTHESIS

CROSS REFERENCE TO RELATED APPLICATIONS

This invention claims benefit of priority to Germany patent application serial number DE 10 2008 043 642.9, filed on Nov. 11, 2008; the contents of which are herein incorporated by reference in their entirety.

FIELD OF THE INVENTION

The present invention relates to an endoprosthesis or implant, in particular an intraluminal endoprosthesis, for example a stent, having a base body composed at least partially of a metallic material, and having a functional element which is attached to the base body or imbedded therein.

BACKGROUND OF THE INVENTION

Stents are endovascular prostheses which may be used for the treatment of stenoses (vascular constrictions). Stents have a base body in the form of a hollow cylindrical or tubular base lattice which is open at both longitudinal ends of the tube. The tubular base lattice of such an endoprosthesis is inserted into the vessel to be treated, and is used to support the vessel.

Such stents or other endoprostheses frequently contain metallic materials in their base body. The metallic materials may form a biodegradable substance which may also contain polymeric biodegradable materials.

The term "biodegradation" refers to hydrolytic, enzymatic, and other metabolic chemical degradation processes in the living organism which are primarily caused by the bodily fluids which come into contact with the endoprosthesis, resulting in gradual dissolution of at least large portions of the endoprosthesis. The term "biocorrosion" is often used synonymously for "biodegradation." The term "bioabsorption" includes the subsequent absorption of the degradation products by the living organism.

Suitable substances (base substances) for the base body of biodegradable endoprostheses may be composed of a number of materials. Examples of suitable polymeric compounds include polymers from the group including cellulose, collagen, albumin, casein, polysaccharides (PSAC), polylactide (PLA), poly-L-lactide (PLLA), polyglycol (PGA), poly-D,L-lactide-co-glycolide (PDLLA-PGA), polyhydroxybutyric acid (PHB), polyhydroxyvaleric acid (PHV), polyalkyl carbonates, polyortho esters, polyethylene terephtalate (PET), polymalonic acid (PML), polyanhydrides, polyphosphazenes, polyamino acids, and the copolymers thereof, as well as hyaluronic acid. Depending on the desired properties, the polymers may be present in pure form, derivatized form, in the form of blends, or as copolymers. Metallic biodegradable materials are based, for example, on alloys of magnesium, iron, zinc, and/or tungsten.

The present invention relates in particular to stents or other endoprostheses having a base body whose material contains a metallic substance. In addition to the biodegradable materials named, noble metals such as platinum, iridium, gold, tantalum, yttrium, zirconium, ytterbium, or the alloys thereof represent suitable metallic substances.

It is known to provide stents with functional elements which have a different material composition, at least in a portion of their volume, compared to the material of the base body. These functional elements are used, for example, to determine the position of a stent in the body or for the release of medicaments.

The position of a stent is often determined by use of imaging methods, for example an X-ray device. Since the materials used for the base body of stents generally absorb only moderate amounts of X-ray radiation, i.e., they are X-ray permeable and/or radiolucent, stents are frequently provided with so-called markers as functional elements which contain a material that absorbs X-rays and/or other electromagnetic radiation (referred to below as radiopaque or X-ray opaque material) more strongly than the material of the base body.

U.S. Pat. No. 6,355,058 B1 describes a stent in which radiopaque markers in the form of particles are contained in a polymeric binder. The binder is distributed (dispersed) on the surface of the stent. Such a distribution of radiopaque particles generally does not provide for sufficient density of these materials, and therefore the radiopacity is too low for many applications.

U.S. Pat. No. 6,293,966 B1 discloses a stent having radiopaque marker elements which on their distal and proximal ends have a C-shaped element which in each case forms an essentially spherical receptacle. Marker elements having spherical end sections are inserted into these receptacles. The spherical end sections are affixed, by means of a positive fit and optionally by means of a weld connection, in the receptacles formed by the C-shaped elements.

DE 698 36 656 T2 illustrates and describes a bioabsorbable marker having radiopaque components for use on an implantable endoprosthesis such as a stent. The bioabsorbable radiopaque markers have, for example, porous sections filled with radiopaque material. A marker is also described which has hollow, cavity-like, porous sections filled with radiopaque material. The prior art also discloses a marker which is designed as an oblong element in the manner of a filament which is looped around sections of the implantable endoprosthesis.

For stents having a base body composed of a metallic material, when functional elements, for example radiopaque elements made of gold or silver, are provided on the base body of the stent the problem of contact corrosion occurs at the contact region between the material of the base body and the material of the functional element. This results in destruction of the stent, or separation of the functional element from the stent structure, so that the endoprosthesis can no longer perform its function, or may not be able to be found. The above-described endoprostheses from the prior art provide no solution to this problem.

SUMMARY OF THE INVENTION

The feature of the present invention, therefore, is to provide an endoprosthesis for which functional elements containing a metallic material do not exhibit the described contact corrosion.

The above feature is achieved by an endoprosthesis in which the functional element is provided with a barrier layer which electrically insulates the radiopaque and/or X-ray opaque material from the base body.

Such an endoprosthesis according to the invention has the advantage that it does not exhibit a battery effect despite combination of various metals, and therefore has no contact corrosion or, for degradable materials, no unwanted degradation (or acceleration of degradation) of the stent. As a result of the barrier layer the functional element, which represents a radiopaque marker, remains for a longer period of time, and may remain permanently in the treated vessel, so that at a later time the functional element still indicates the implantation site of the endoprosthesis, for example even when the endoprosthesis is already partially degraded.

In one preferred exemplary embodiment, the barrier layer completely encloses the functional element. This results in particularly effective insulation of the functional element.

In a further exemplary embodiment of the invention, the barrier layer contains one or more materials from the group including parylene, preferably parylene C, polyzene F, silicone, gycocalyx, diamond-like carbon (DLC), cyanoacrylates (in particular methyl-2-cyanoacrylate, n-butyl cyanoacrylate, and 2-octyl-cyanoacrylate), and titanium dioxide. In general, other nonconductive, permanently hydrophobic polymers are also suitable. The referenced compounds have a particularly good electrical insulating effect, and are also characterized by low water permeability and a high degree of permanence and biocompatibility. These properties are particularly advantageous for use as endoprostheses. The thickness of the barrier layer is preferably between approximately 1 μm and approximately 20 μm.

In this context, "parylene" refers to completely linear, partially crystalline, uncrosslinked aromatic polymers. Depending on their structure, these polymers may be divided into four different basic types: parylene C, parylene D, parylene N, and parylene F. Parylene may be applied to the functional element, preferably using a plasma-chemical coating process.

The functional element preferably has one or more radiopaque elements or compounds from the group including platinum, iridium, gold, tungsten, tantalum, yttrium, zirconium, ytterbium, alloys of these metals, and iodine compounds.

To provide a volume, i.e., extension, of the functional element which results in sufficient radiopacity, in one preferred exemplary embodiment the barrier layer encloses a volume of the radiopaque material of a functional element with a cross-sectional area of at least approximately 200 μm×approximately 100 μm. For good radiopacity, the extension of the cross-sectional area in at least one dimension (direction) should ideally be at least approximately 300 μm. The referenced cross-sectional area or extension in one dimension may also be achieved by two or more functional elements which are correspondingly situated close to one another. The extension or the volume of the functional element should in particular be selected to be large enough that the extension or volume encompasses at least two pixels of the resolution of common angiography devices.

The functional element is preferably joined to the barrier layer by means of a positive fit connection and/or an adhesive bond to the base body. These connections are particularly easy to establish. When cyanoacrylate is used in the barrier layer, it may also provide the function of the adhesive bond.

As stated above, the base body preferably contains a biodegradable material, preferably magnesium and/or a magnesium alloy.

It is particularly easy to affix functional elements to the base body when the functional elements have at least one through opening for attachment to the base body. Alternatively or additionally, the functional elements may provide [sic; be provided with] a circumferential groove for attachment to the base body.

The functional elements may likewise be easily affixed to the base body when the functional element together with the barrier layer has a wire-shaped design. In this case, such functional elements are preferably affixed parallel to a structure of the base body.

Furthermore, it is advantageous for the geometry of the functional element and/or the connection of the functional element to the base body to be selected in such a way that the activity of the endoprosthesis, preferably the stent, is not greatly impaired with regard to the clinical supporting effect after crimping, tracking, or dilation. Likewise, the aim is to facilitate complete growth into the treated vessel (neointima formation). In this regard the flow of bodily fluid must not be hindered. Therefore, in one preferred exemplary embodiment the functional element is not allowed to project into the stent lumen. For this purpose the functional element should have a non-circular or non-oval full cross section in at least one direction, thus preventing complete blockage of a vessel. Polygonal functional elements or functional elements with pronounced through holes, for example, are suitable. If possible, the functional elements are also situated at the end position, i.e., at one or both ends in the longitudinal direction of the endoprosthesis, since in this case the end points of the endoprosthesis may be easily identified in the X-ray image.

The invention is explained in greater detail below with reference to exemplary embodiments illustrated in the figures. All features which are described and/or graphically illustrated constitute subject matter of the invention, regardless of their summary in the claims or back references.

DETAILED DESCRIPTION OF THE INVENTION

Figure 1:
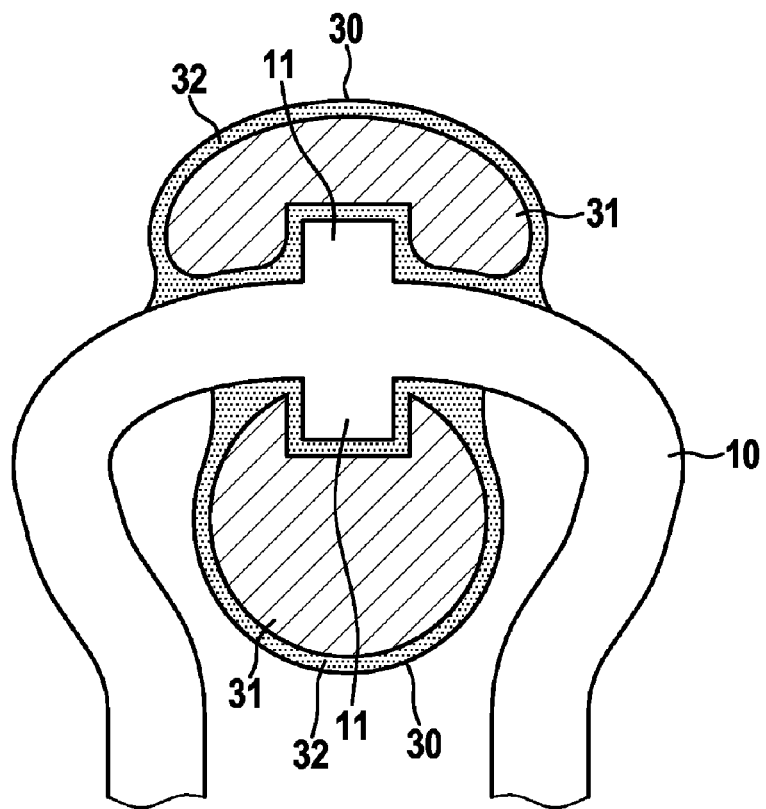
FIG. 1 shows a longitudinal section of a first exemplary embodiment of an endoprosthesis according to the invention.

FIG. 1 shows a section of a base body designed as a lattice in a first exemplary embodiment of an endoprosthesis according to the invention embodied as a stent. The base body has webs folded in a zigzag or meandering manner and extending essentially in the circumferential direction or helically as support elements 10, and has webs extending essentially in the longitudinal direction of the stent as connecting elements 20 (see FIG. 4). The section illustrated in FIG. 1 is part of a support element 10. As a whole, the stent is designed as a tubular or hollow cylindrical endoprosthesis which is open at the ends and extends in the direction of the connecting webs 20.

In the region of an essentially circular section, the support element 10 has finger-shaped sections 11 which extend in the longitudinal direction of the stent. At each finger-shaped section 11 a functional element 30 is provided which has a core 31 composed of radiopaque (X-ray opaque) material such as platinum, iridium, gold, tungsten, tantalum, yttrium, zirconium, ytterbium, or alloys of these metals, or an iodine compound. The core 31 of the functional element 30 is completely enclosed by a barrier layer 32 which is composed of parylene C, for example.

Figure 2:
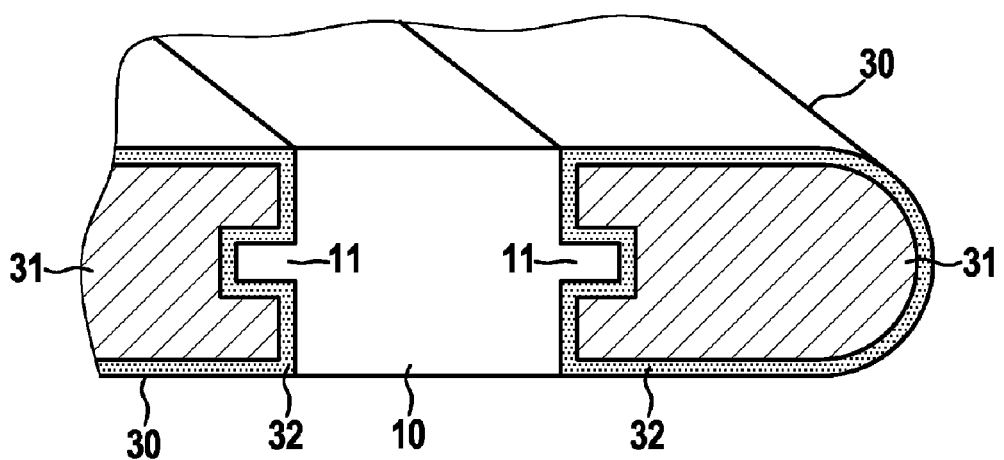
FIG. 2 shows a cross section of the exemplary embodiment according to FIG. 1.

The barrier layer 32 is positioned in particular in such a way that it is located between the core 31 containing the metallic base material and the support element 10, or between the core 31 and the finger-shaped element 11, and electrically insulates the core from the support element 10 and from the finger-shaped element 11. The material of the barrier layer 32 is also designed to be biocompatible. In the exemplary embodiment illustrated in FIGS. 1 and 2, the functional element 30 is affixed to the support element 10 and the finger-shaped elements 11 by means of an adhesive bond.

Figure 3:
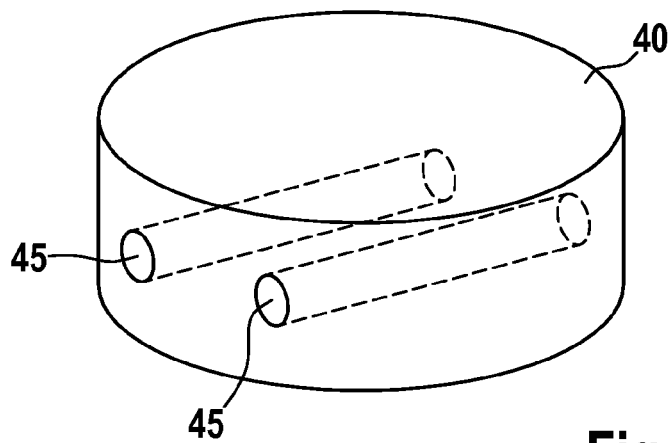
FIG. 3 shows a functional element for a second exemplary embodiment of an endoprosthesis according to the invention, in a perspective view from the side.

FIG. 3 shows an essentially cylindrical functional element 40 having two cylindrical through openings 45. The functional element 40 is completely enclosed by a barrier layer, analogously to the functional elements 30 illustrated in FIGS. 1 and 2. In addition, the barrier layer is configured so that it completely encloses the through openings. For this purpose, for example, the barrier layer completely covers the cylindrical shell inner faces of the openings 45.

Figure 4:
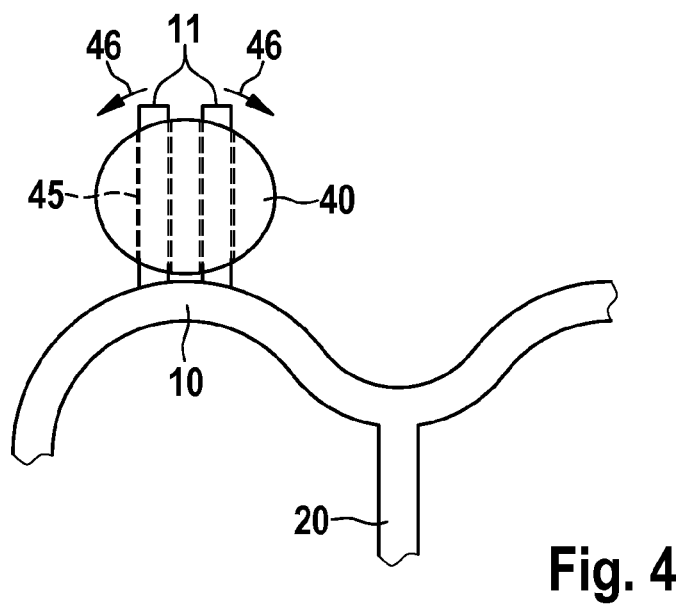
FIG. 4 shows the second exemplary embodiment of an endoprosthesis according to the invention, in a view from the side.

FIG. 4 shows the manner in which the functional element 40 may be provided on a support element 10. For this purpose the support element 10 has two finger-shaped elements 11 which are made of the material of the base body and which project away from the support element 10 in the longitudinal direction of the stent. The finger-shaped elements have a rotatable and/or bendable design. After the functional element 40 has been provided with a barrier layer (see description for FIG. 3), it is placed on the finger-shaped elements 11 in such a way that the latter come to rest in the openings 45. The functional element 40 is affixed to the stent by rotating the finger-shaped elements 11 about their axis and/or by slightly bending them outward (see arrow 46). When bending is used, the attachment is a force-fit connection.

Figure 5:
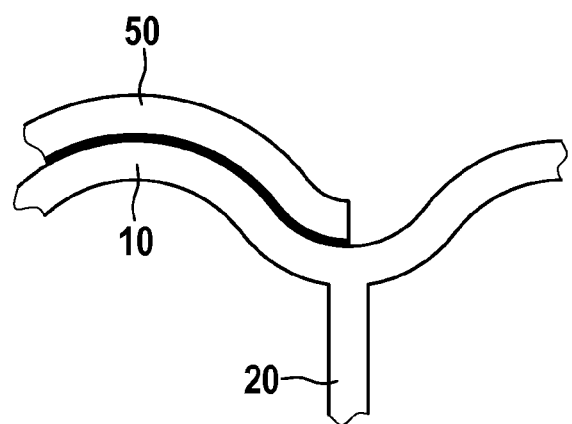
FIG. 5 shows a third exemplary embodiment of an endoprosthesis according to the invention, in a view from the side.

The further exemplary embodiment of an endoprosthesis according to the invention illustrated in FIG. 5 shows a section of the stent having a support element 10 and a connecting web 20, the support element 10 being provided with an essentially wire-shaped functional element 50. The functional element 50 has an essentially cylindrical core made of an X-ray opaque material which is completely enclosed by a barrier layer. The wire-shaped functional element 50 is affixed to the support element 10 of the stent by means of an adhesive bond, for example. The wire-shaped functional element follows the contour of the support element 10. So as not to hinder crimping and/or dilation of the endoprosthesis if such is necessary, it is advantageous for the wire-shaped functional element 50 to be attached to the support element 10 solely via a point adhesive bond, and/or for the wire-shaped functional element 50 to be made of an easily bendable, for example a suitably thin, material.

Figure 6:
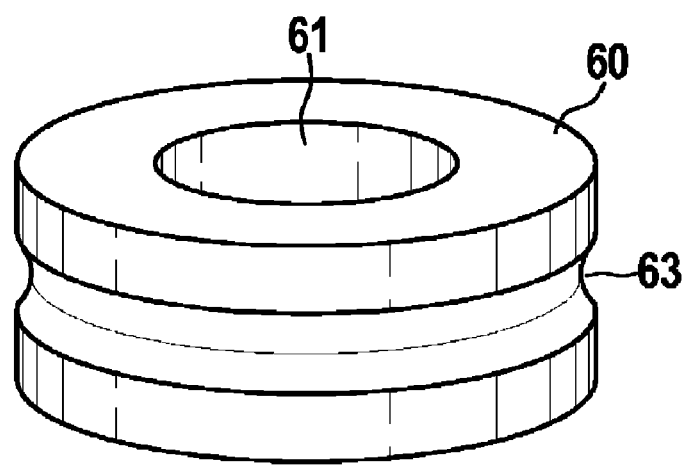
FIG. 6 shows a functional element for a fourth exemplary embodiment of an endoprosthesis according to the invention, in a perspective view from the side.

FIG. 6 shows the functional element 60 for a further exemplary embodiment of an endoprosthesis according to the invention. The functional element 60 is designed as a hollow cylinder having an X-ray opaque core and a barrier layer which completely encloses the core, the functional element 60 having a cylindrical through opening 61. A circumferential groove 63 is provided on the lateral surface of the functional element 60 which is used for attaching the functional element 60 to the stent. In a further exemplary embodiment the functional element 60 may be used without the through opening 61.

Figure 7:
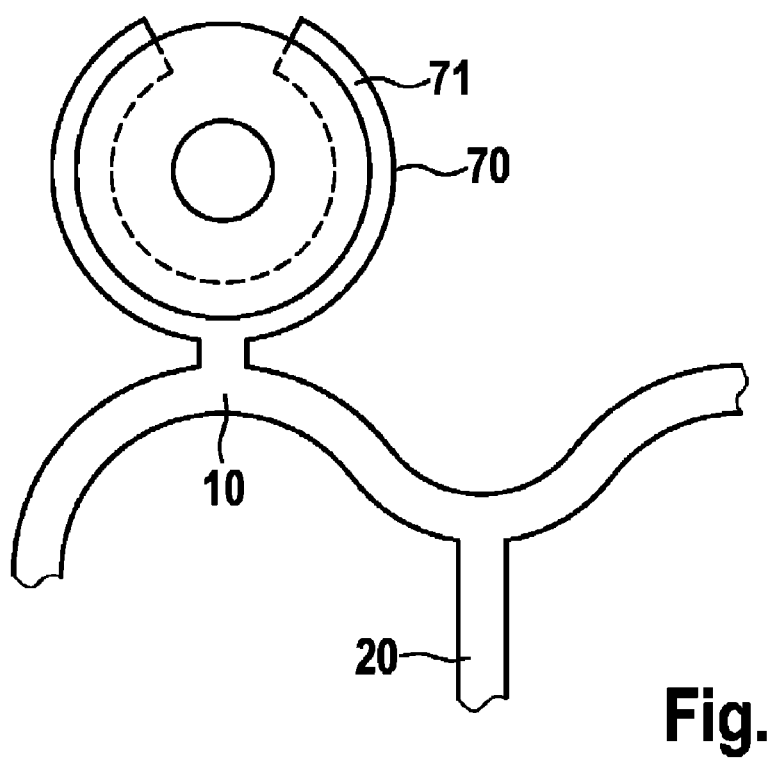
FIG. 7 shows the fourth exemplary embodiment of an endoprosthesis according to the invention, in a view from the side.

This attachment to a support element 10 of the stent is illustrated in FIG. 7. A forked element 70 used to accommodate the functional element 60 is provided on the support element 10. The forked element 70 forms an annular section 71 which is situated in the groove 63 when the functional element 60 is attached to the stent. The functional element 60 may also be securely affixed to the stent by providing one or more point adhesive bonds, also for tracking.

The exemplary embodiments described above for attaching the functional elements to an endoprosthesis in the form of a stent show only a few possibilities by means of which a functional element having a barrier layer may be easily joined to the base body. However, the present invention is not limited to these attachment possibilities. In particular, the functional element may be provided only in the regions having a barrier layer, or in regions where the functional element is joined to the base body of the endoprosthesis, or, for a connection to the base body, in regions where the functional element would directly contact the base body in the absence of a barrier layer. It is not necessary in every case for the radiopaque metallic material (core) of the functional element to be completely enclosed.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

LIST OF REFERENCE NUMERALS

10 Support element
11 Finger-shaped section
20 Connecting web
30 Functional element
31 Core
32 Barrier layer
40 Functional element
45 Cylindrical opening
50 Functional element
60 Functional element
61 Cylindrical opening
63 Groove
70 Forked element
71 Annular section

What is claimed is:

1. An endoprosthesis having a base body composed at least partially of a metallic material, and having a functional element which is attached to the base body or imbedded therein and which contains material that is radiopaque and/or X-ray opaque and has a different material composition, at least in a portion of its volume, compared to the material of the base body, characterized in that:
    the functional element comprises two through openings and a barrier layer which electrically insulates the radiopaque and/or X-ray opaque material from the base body; and
    the base body comprises two finger elements that extend entirely through the through openings on a same functional element and are bent or rotated outward from the through openings.

2. The endoprosthesis according to claim 1, characterized in that the barrier layer completely encloses the radiopaque or X-ray opaque material.

3. The endoprosthesis according to claim 1, characterized in that the barrier layer contains one or more materials selected from the group consisting of a parylene, parylene C, polyzene F, silicone, gycocalyx, diamond-like carbon (DLC), a cyanoacrylate, methyl-2-cyanoacrylate, n-butyl cyanoacrylate, 2-octyl-cyanoacrylate, and titanium dioxide.

4. The endoprosthesis according to claim 1, characterized in that the barrier layer encloses a volume of the radiopaque and/or X-ray opaque material of one or more adjacent functional elements with a cross-sectional area of at least approximately 200 μm by approximately 100 μm, and/or with an extension in one direction of at least approximately 300 μm, and/or with an extension corresponding to two pixels resolution of angiography devices.

5. The endoprosthesis according to claim 1, characterized in that the base body contains a biodegradable material comprising magnesium and/or a magnesium alloy.

6. The endoprosthesis according to claim 1, characterized in that the functional element together with the surrounding barrier layer has a wire-shaped design.

7. The endoprosthesis according to claim 1, characterized in that the two finger elements are made of the same material as the base body.

8. The endoprosthesis according to claim 5, characterized in that the two finger elements are made of the same material as the base body.

9. An endoprosthesis having a base body composed at least partially of a metallic material, and having a functional element which is attached to the base body or imbedded therein and which contains material that is radiopaque and/or X-ray opaque and has a different material composition, at least in a portion of its volume, compared to the material of the base body, characterized in that:
the functional element comprises a hollow cylinder with an opaque core and a barrier layer that completely encloses the core, which electrically insulates the radiopaque and/or X-ray opaque material from the base body, the functional element further comprising a circumferential groove on a lateral surface; and
the base body comprises a forked element comprising an annular section that is situated in the circumferential groove.

10. The endoprosthesis according to claim 9, characterized in that the barrier layer contains one or more materials selected from the group consisting of a parylene, parylene C, polyzene F, silicone, gycocalyx, diamond-like carbon (DLC), a cyanoacrylate, methyl-2-cyanoacrylate, n-butyl cyanoacrylate, 2-octyl-cyanoacrylate, and titanium dioxide.

11. The endoprosthesis according to claim 9, characterized in that the barrier layer encloses a volume of the radiopaque and/or X-ray opaque material of one or more adjacent functional elements with a cross-sectional area of at least approximately 200 μm by approximately 100 μm, and/or with an extension in one direction of at least approximately 300 μm, and/or with an extension corresponding to two pixels resolution of angiography devices.

12. The endoprosthesis according to claim 9, characterized in that the base body contains a biodegradable material comprising magnesium and/or a magnesium alloy.

13. The endoprosthesis according to claim 12, characterized in that the forked element is made of the same material as the base body.

14. The endoprosthesis according to claim 9, characterized in that the forked element is made of the same material as the base body.

* * * * *